United States Patent [19]

Rubio Salas

[11] 4,419,229

[45] Dec. 6, 1983

[54] DEVICE FOR CONTROLLING THE CATION SATURATION IN INTERCHANGING FILTERS

[75] Inventor: Roque Rubio Salas, Barcelona, Spain

[73] Assignee: Bayard J. R. International S.A., Barcelona, Spain

[21] Appl. No.: 337,272

[22] Filed: Jan. 5, 1982

[30] Foreign Application Priority Data

Nov. 10, 1981 [ES] Spain .............................. 261.311[U]

[51] Int. Cl.³ .............................................. C02B 1/40
[52] U.S. Cl. ..................................... 210/85; 210/96.1
[58] Field of Search ................................ 210/85, 96.1

[56] References Cited

U.S. PATENT DOCUMENTS

| | | | |
|---|---|---|---|
| 3,172,037 | 3/1965 | Pfeiffer | 210/96.1 |
| 3,245,537 | 4/1966 | Burgess | 210/96.1 |
| 3,252,578 | 5/1966 | Smith et al. | 210/85 |
| 3,282,426 | 11/1966 | Entringer | 210/96.1 |
| 3,768,649 | 10/1973 | Fleckenstein | 210/96.1 |
| 3,869,382 | 3/1975 | Tejeda | 210/96.1 |
| 4,082,666 | 4/1978 | Jones et al. | 210/96.1 |

Primary Examiner—John Adee
Attorney, Agent, or Firm—Wenderoth, Lind & Ponack

[57] ABSTRACT

A device for detecting cation saturation in an ion exchange filter includes electrodes disposed in an interchanging resin. One of the electrodes receives power from a source of supply, while the other electrode picks up a cation potential signal and through a tracking circuit comprising an operational system informs a comparator circuit having a fixed threshold valve which operates depending on the value emitted by the tracking circuit, activating a luminous and/or acoustic alarm system, all of which is optatively activated by means of a manually operated push-button.

1 Claim, 2 Drawing Figures

U.S. Patent  Dec. 6, 1983  4,419,229
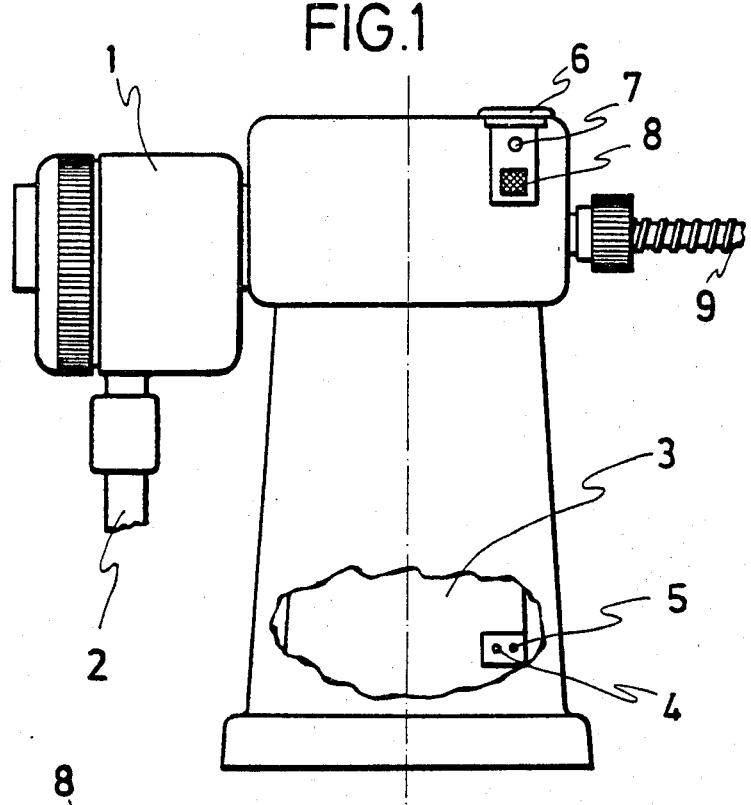
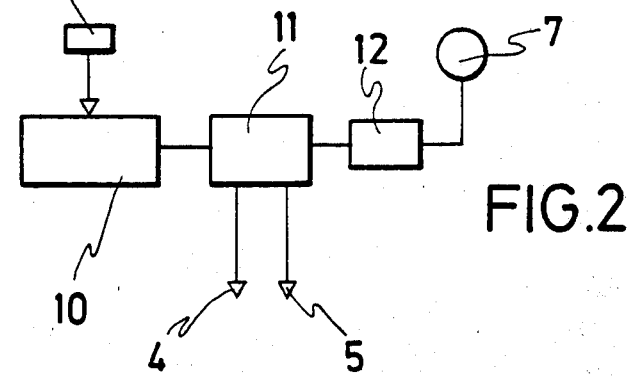

DEVICE FOR CONTROLLING THE CATION SATURATION IN INTERCHANGING FILTERS

BACKGROUND OF THE INVENTION

The present invention relates to a device for controlling cation saturation, especially designed to verify the state of activity of the ion interchanging or exchange resins in drinking water purifying filters, by measuring the cation potential maintained by the resins after a period of use.

Consumers are becoming more and more interested in filters for purifying drinking water, both in those cases in which the water is supplied from a municipal network and in those in which it is supplied by their own means, whether from a well or from a spring. In any event the water should be chlorinated to avoid infections and in the majority of the cases it should be treated with softening agents capable of eliminating excess calcium.

Clearly the purifying filter is an effective and cheap solution since it simultaneously treats the negative points of the water, taste and excessive hardness. The incorporation of biological filters eliminates possible chlorination-resistant bacteria, finally obtaining a clear water having a pleasant taste which is perfect for human consumption.

The deodorization and removal of the taste of the water is carried out with the help of activated carbon. However, the hardness of the calcium is reduced by interchanging or exchange resins, the effectiveness of which must be controlled and which is not readily recognized.

The regeneration of the ion exchange resins is carried out with diluted salt, restoring the softening properties of the water. The activated carbon is regenerated subjecting it to the action of heat in a furnace. However, the duration of the exchange resin, after a finite number of regenerations, coincides in practice with the duration of the activated carbon and in view of the low cost thereof, both components are simultaneously replaced thus to facilitate the handling and potential yield thereof, they are used in a combined form in the majority of the cases.

Thus, there remains the problem of determining exactly the exchange capacity of the resins, wherefore apparatus for measuring the electric conductivity, the effectiveness of which is doubtful in spite of the high cost thereof, are commonly used.

SUMMARY OF THE INVENTION

The object of the invention is to provide a device for controlling the effectiveness of the resins, measuring the saturation of the cations and operating a signalling device when the result of the measurement is not satisfactory. Such signalling device produces a luminous and/or sound effect and, therefore, no reading nor indication of an oscillating needle on a dial need be interpreted by the user.

This object is achieved according to the invention by providing a device operable to determine the degree of saturation of cations in resin exchange filters. The device includes electrodes disposed in the exchange resin, one of which is connected to an electric power source to receive power therefrom, while the other picks up the cation potential signal and through a tracking circuit which comprises an operational system, informs a fixed threshold comparator circuit which operates depending on the value emitted by the tracking circuit, activating or not a luminous and/or acoustic alarm system.

The operation motivating the activation of the device can be carried out automatically through an adjustable timer device. However, from an economical and practical point of view, it is more advantageous to carry it out by means of a manual push-button.

BRIEF DESCRIPTION OF THE DRAWINGS

The invention will be described in more detail below with reference to the accompanying drawings, wherein:

FIG. 1 is an elevation view of a purification device; and

FIG. 2 is a circuit diagram of the device.

DETAILED DESCRIPTION OF THE INVENTION

Referring to the drawings, the purifier comprises a bacteriological filter unit 1 which receives water through a duct 2 and directs it through an inner distributor to a bed of interchanging resins 3, after having passed through activated carbon, to finally be discharged through a pipe 9.

The bed 3 is provided with electrodes 4, 5 which, by means of a wiring, are joined to a circuit plate situated below a battery/holding 6 and close to a luminous alarm 7 disposed close to a push-button 8.

An electric power 10 is activated by the push-button 8 and feeds an assembly in which a tracking device 11 includes the electrodes 4, 5, and connects to a comparator 12 having a threshold valve, which when exceeded causes activation of luminous alarm 7.

The source 10 can be a 9-volt battery or a conventional transformer-rectifier assembly. Such source supplies the system with power. And it can even have a test pilot of the operative.

The purpose of the tracking circuit 11 is to receive the information from the electrodes, one of which, 4 for example, is connected to the source 10, while the other 5 supplies an impedance signal to the tracking circuit 11 which isolates the measuring system and informs the comparator 12 provided with a signal threshold which, when exceeded, connects and activates the alarm 7.

The tracking circuit 11 comprises an operational system having a circuit of resistances and an operational amplifier which prevents outside disturbances.

The comparator 12 is comprised of another operational amplifier having an adjustable trip signal which operates when the threshold determined by the resistances is exceeded, permitting a signal, which activates the optic or sound signalling means 7, to pass.

I claim:

1. In a water treatment apparatus of the ion exchange type and including a bed of ion exchange resins, and means for determining the relative degree of saturation of said resins, the improvement wherein said determining means comprises means for detecting a predetermined reduction in the ion exchange capacity of said resins, said detecting means comprising:

a source of electric power;

a first electrode positioned within said resin bed and electrically connected to said power source for receiving therefrom a potential signal;

a second electrode positioned within said resin bed, without being electrically connected to said power source, for providing a potential signal representative of the ion exchange capacity of said resins;

tracking circuit means, connected to said first and second electrodes, for receiving said signals from said first and second electrodes and for generating a difference signal representative of the difference in potential therebetween;

comparator means, connected to said tracking circuit means and having a threshold value representative of a predetermined reduction in the ion exchange capacity of said resins, for receiving said difference signal from said tracking circuit means, for comparing said difference signal with said threshold value, and for generating an activating signal when said difference signal exceeds said threshold valve; and alarm means, connected to said comparator means, for receiving and being activated by said activating signal, thereby generating an alarm indicative of the occurrence of a predetermined reduction in the ion exchange capacity of said resins.

* * * * *